United States Patent [19]
Blake, III

[11] Patent Number: 5,338,294
[45] Date of Patent: Aug. 16, 1994

[54] UROLOGICAL EVACUATOR

[75] Inventor: Joseph W. Blake, III, Norwalk, Conn.

[73] Assignee: Jack Kaufman, Merrick, N.Y.; a part interest

[21] Appl. No.: 900,677

[22] Filed: Jun. 19, 1992

[51] Int. Cl.$^5$ .............................. A61M 5/00
[52] U.S. Cl. .................... 604/38; 604/190; 604/236; 604/237
[58] Field of Search .................. 604/36–38, 604/121, 190, 218, 236, 237

[56] References Cited

U.S. PATENT DOCUMENTS

| | | | |
|---|---|---|---|
| 1,265,537 | 5/1918 | Shull | 604/218 |
| 1,348,412 | 8/1920 | Harriman | 604/218 |
| 2,263,865 | 11/1941 | Bailen | 604/218 |
| 3,747,812 | 7/1973 | Karman et al. | 604/236 |
| 3,938,513 | 2/1976 | Hargest | 604/190 |
| 4,066,079 | 1/1978 | Chiarolla | 604/190 |
| 4,210,173 | 7/1980 | Choksi et al. | 604/236 |
| 4,332,249 | 6/1982 | Joslin | 604/36 |
| 4,801,292 | 1/1989 | Watson | 604/36 |
| 4,820,276 | 4/1989 | Moreno | 604/190 |

FOREIGN PATENT DOCUMENTS

| | | | |
|---|---|---|---|
| 675740 | 2/1930 | France | 604/218 |
| 8400011 | 1/1984 | PCT Int'l Appl. | 604/187 |

*Primary Examiner*—Ralph Lewis
*Attorney, Agent, or Firm*—Patrick J. Walsh

[57] ABSTRACT

An evacuator particularly suited for irrigation and removal of tissue from a body cavity such as the bladder. The evacuator includes a positive displacement syringe with a hollow plunger for pumping a sterile solution into the bladder for irrigation and for withdrawing the solution and entrained tissue from the bladder and urethra. Internal valving controls the order of flow within the evacuator so that, as the solution circulates through the evacuator, tissue is filtered from the solution and captured in a collection container.

12 Claims, 4 Drawing Sheets

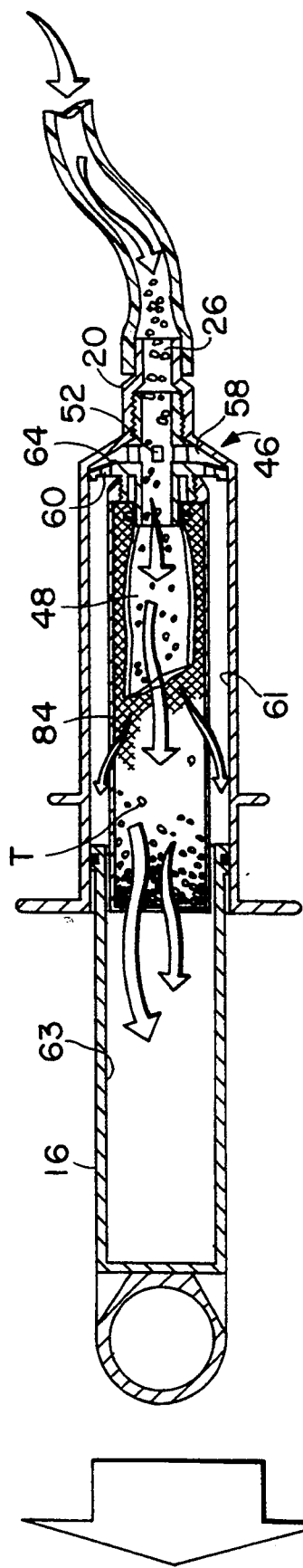
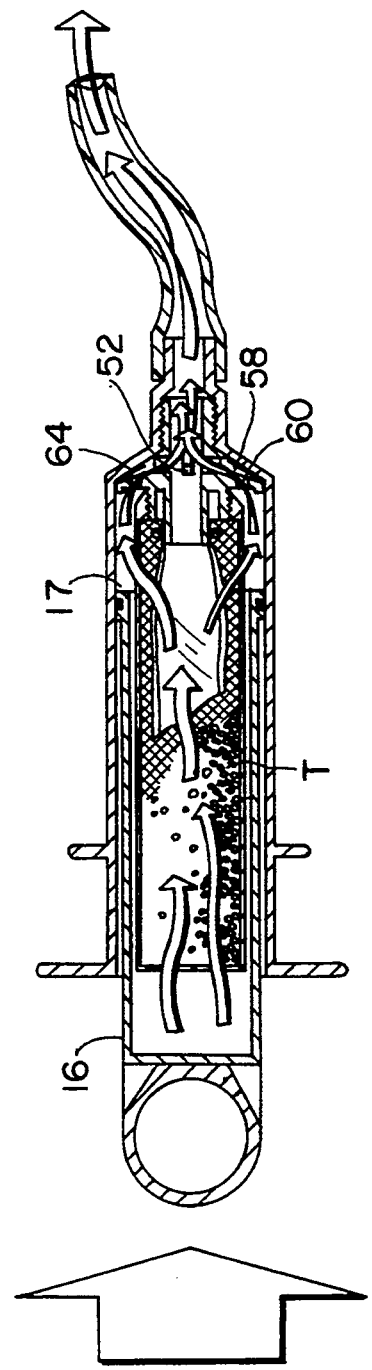

UROLOGICAL EVACUATOR

BACKGROUND OF THE INVENTION

The present invention relates to medical irrigation and aspiration syringes and particularly to urological irrigator-evacuator syringes especially suited for use with a resectoscope in performing a transurethral prostatectomy.

In a medical procedure of this kind, the bladder is prefilled with a sterile solution and the bladder and urethra are evacuated periodically to draw out tissue excised from the prostate. Other tissue present in the bladder such as stones and so forth may also be evacuated. It is desirable to collect evacuated tissue for examination by the surgeon and for laboratory analysis as to the condition of the tissue. An evacuator such as the standard Ellik evacuator is used for irrigating and evacuating the bladder and for collecting tissue. The Ellik evacuator is simple and practical and consists of an hour-glass shaped bowl with a rubber bulb and nozzle fitted to the upper bowl for circulating solution through the urethra and bladder. Tissue entrained in the return flow of solution is to be collected in the lower chamber. It is a limitation of the Ellik evacuator that entrained tissue must settle by gravity in a solution of nearly the same density. There is also the tendency for a portion of the tissue to be carried back into the bladder with recirculation of the solution.

A number of prior art devices have been developed as improvements to the Ellik evacuator with particular attention to the task of efficient separation of tissue from recirculated solution.

U.S. Pat. No. 4,801,292 to Watson discloses a medical pump for debris collection including a bulb or squeeze-type syringe for pumping flushing liquid into the bladder. Bladder efflux returns to the syringe and flows through a basket filter where tissue is trapped for removal and analysis. Efflux continues flowing through the porous filter wall through a first one-way valve and into the squeeze bulb chamber. Recirculation occurs by squeezing the bulb and pressurizing the liquid which now follows a separate path out of the syringe through a second one way valve. The Watson device has an open top end in the basket filter and relies on gravitational force for settling and retention of tissue fragments in the basket. Accordingly, Watson is limited to a vertical orientation of the pump with squeeze bulb lowermost in order to properly collect tissue fragments. Additionally, the gravitational settling of tissue in the sterile solution is time consuming, and any fragments floating in the vicinity of the nozzle are likely to be carried back into the bladder on a subsequent compression of the squeeze bulb.

U.S. Pat. No. 3,892,226 to Rosen discloses a urological irrigation-evacuator including a squeeze bulb for circulating sterile solution for irrigating of the bladder. A specimen collecting receptacle for accumulating tissue washed from the bladder is affixed to the syringe by means of a vertically depending two-way flow conduit. Bladder efflux carrying tissue flows down one conduit path toward the receptacle so that tissue is filtered out of the efflux and collected in the receptacle. The resulting device is cumbersome requiring two-hand operation as well as a considerable volume of solution to fill the two-way conduit and receptacle. The filter consists of a grille in the two-way conduit which is insufficient for effective filtering.

U.S. Pat. No. 4,282,873 to Roth discloses a medical irrigation syringe in which a hollow bulb pump is rotatably mounted to the syringe body so that the irrigating fluid may be pumped directly into and out of a resectoscope or through a circuitous path via a collection receptacle attached to the pump for filtering out tissue. A filter screen is provided along the circuitous path for accumulating tissue which thereafter settles into an open receptacle. Roth requires two-handed operation, and while screening tissue out of the circulation liquid, does not provide means for trapping and segregating tissue from the solution.

U.S. Pat. No. 4,729,764 to Gaultier discloses an irrigator and separator similar in operating principle to the Rosen and Roth patents in providing a circuitous path for sterile fluid carrying tissue evacuated from a body cavity. The evacuated fluid is drawn out and through a filter screen where tissue is retained in a collection chamber. The filtered fluid then returns to the syringe pump chamber. The Gaultier device requires two-hand operation, is cumbersome, and requires a substantial liquid volume to fill the pump and collection chambers.

There remains a need for an evacuator which is simple and practical to use and which efficiently filters and captures tissue entrained in a lavage solution.

SUMMARY OF THE INVENTION

The present invention provides a urological evacuator for irrigation and removal of tissue from a body cavity such as the bladder. The evacuator pumps a sterile solution into the bladder for irrigation and withdraws the solution carrying tissue from the bladder and urethra. The solution circulates through the evacuator where tissue is filtered from the solution and captured in a collection container.

In accordance with the invention, the evacuator comprises a syringe including a barrel and plunger assembly for containing and circulating the sterile solution, an interior container for filtering the solution to remove and contain tissue fragments evacuated from the bladder, and interior valving providing for circulation of solution into the bladder as the plunger is depressed, and for evacuation and filtration of tissue from solution through the interior container as the plunger is withdrawn. An inlet valve for evacuated solution and tissue comprises a flapper valve which is opened by the efflux stream therethrough as the plunger is withdrawn. The inlet flapper valve collapses from externally applied pressure as when the plunger pressurizes solution within the syringe barrel thereby closing the valve and trapping filtered tissue within the collection container. An outlet valve comprising a disc valve with a plurality of outlet ports opens to permit flow of filtered solution into the bladder. A valve ring comprising an annular web confronts the outlet ports permitting flow out of the syringe through the nozzle when the plunger is depressed. When the plunger is withdrawn to create an efflux, the return flow of solution closes the annular web preventing backflow through the valve ring and directing flow through the inlet flapper valve.

An evacuator according to the invention includes a hollow plunger having a dual telescoping characteristic. The plunger telescopes within the syringe barrel and telescopes over the tissue collection container and inflow control valve located in the barrel. This compact and highly efficient arrangement provides for the irrigation and evacuation flow of the solution according to principles of positive displacement. By depressing the plunger solution flows into and irrigates the bladder. Withdrawal of the plunger induces return flow of tissue laden solution through the inlet valve and into the filter container where the tissue remains. By repeating the irrigation-evacuation cycle substantially all tissue fragments are trapped and collected for inspection and analysis.

The evacuator may be taken apart by removal of the plunger for access to the tissue container for analysis of the tissue. The container Will drain of solution as it is removed from the syringe a feature of the invention that simplifies the task of retrieving the tissue for identification and shipment to a laboratory. Indeed, the tissue may be left untouched in the container for this purpose.

In one embodiment of the invention, only the tissue collection container with inlet end open maybe removed from the evacuator. In another embodiment, the container along with the inlet flapper valve may be removed. In the latter embodiment the flapper valve serves as a closure for the inlet end of the container during removal and subsequent handling.

As a result of the unique dual telescoping characteristic, the evacuator has the same look and feel as well as ease of operation of a standard syringe. The invention results in a syringe which is simple and practical to use and which efficiently and quickly separates tissue from solution. Moreover, the evacuator can perform double use as a Toomey evacuator functioning as an irrigation syringe with or without a collection container.

OBJECTS OF THE INVENTION

It is an object of the invention to provide a urological evacuator which has the look, feel, and ease of operation of conventional syringes.

It is an object of the invention to provide a urological evacuator having a hollow plunger for positive displacement pumping action, accommodating internal components of the evacuator, and for enlarging the internal fluid volume of the evacuator without enlarging its external dimensions.

It is a further object of the invention to provide a urological evacuator for screening and collecting tissue fragments from a circulating solution without interfering with flow of the solution within the evacuator.

It is a further object of the invention to provide a container for receiving filtered tissue and for holding the tissue until the container is removed from the evacuator.

It is a further object of the invention to provide a container for filtered tissue which drains on removal from its syringe.

It is a further object of the invention to provide an evacuator which may easily be disassembled.

Another object of the invention is to provide an evacuator which is not position sensitive and can be used in any convenient orientation.

It is another object of the invention to provide a urological evacuator of robust, economical construction for discarding after single use or, if desired, for repeated use after sterilization.

Another object of the invention is to provide an evacuator of multiple utility including uses normally requiring an Ellik evacuator or a Toomey evacuator.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which:

FIGS. 7 and 8 are schematic views, respectively, of the inlet flow of solution and tissue into the evacuator, and the outlet flow of solution from the evacuator.

DETAILED DESCRIPTION OF THE INVENTION

Figure 1:
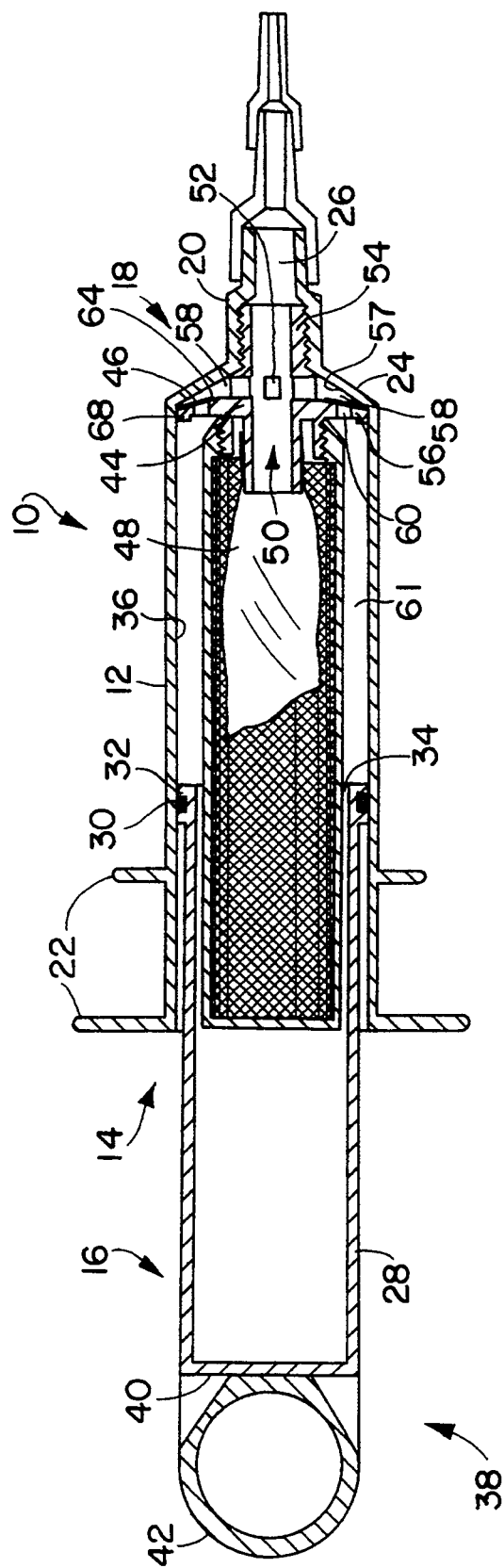
FIG. 1 is a longitudinal section view of a preferred embodiment of the invention.
Figure 2:
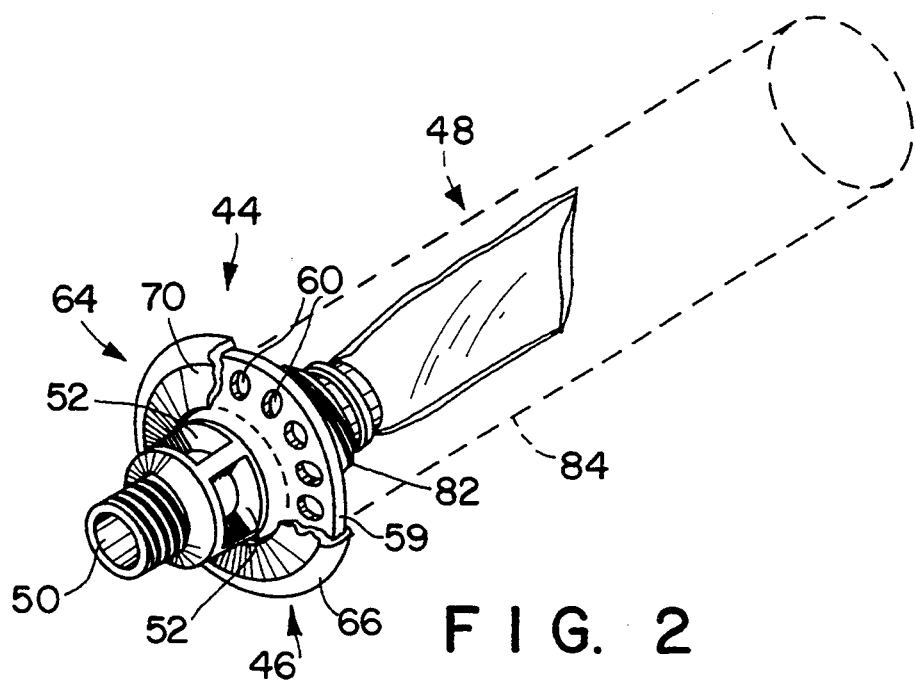
FIG. 2 is an enlarged perspective view partly in section of a preferred valving arrangement for the evacuator.

Referring now to the drawing, the evacuator 10 shown in FIG. 1 includes a generally cylindrical syringe barrel 12 having an open end 14 for receiving a plunger 16 in telescoping relationship therein, and an inlet/outlet end 18 fitted with a nozzle 20. The outer surface of the barrel near the open end is provided with spaced rings 22 for gripping the evacuator between the index and middle fingers. Preferably, the rings are elliptical. The nozzle end of the barrel is defined by a disc-like conical shoulder 24 fitted with forwardly projecting nozzle 20 defining an axial passage 26 for flow of solution into and out of the barrel during use.

The plunger is a hollow cylinder 28 telescoping into the barrel and having a sealing ring 30 fitted into an annular groove 32 at the open end 34 of the plunger. The sealing ring forms a fluid tight seal with the interior surface 36 of the barrel. The sealing action is sufficient to preserve the partial vacuum within the barrel created by withdrawing the plunger, as well as the overpressure generated on a contained solution when the plunger is depressed into the barrel. The opposite end 38 of the plunger is enclosed by an end member 40 having an integral thumb ring 42 for manipulating the plunger. Preferably, the plunger cylinder, end member, and thumb ring are formed in one-piece construction. The thumb ring 42 and the elliptical finger rings 22 facilitate gripping the evacuator as well as moving the plunger within the barrel during use of the evacuator.

The order of flow of solution into and out of the evacuator is determined by a subassembly of a valve flange 44 and first 46 (outlet) and second 48 (inlet) one-way valves (FIGS. 1–4b) positioned in the barrel behind the nozzle. The valve flange provides passageways 50, 52 for the solution and positions the inlet and outlet valves for directing solution flow in cooperation with inward and outward movement of the plunger.

The valve flange is of generally tubular construction having central passageway 50 for solution flow. As best shown in FIG. 1, the valve flange is secured to the front opening 18 of the barrel 12 in alignment with the nozzle 20. The forward nipple portion 54 of the valve flange may be threaded for this purpose. A sloping shoulder 56 on the valve flange abuts the nozzle and spaces the flange from the inner shoulder surface 57 of the barrel defining therebetween an annular flow chamber 58 from the exterior to interior of the valve flange via circumferentially spaced ports or passageways 52.

The valve flange further includes a first control valve 46 in the form of a radially projecting valve disc 59 extending circumferentially of the flange and having therein a plurality of longitudinally extending apertures or passageways 60 providing for outward flow of solution from the interior 61 of the barrel through annular chamber 58 and ports 52 into the central passageway 26. A valve diaphragm 64 (FIGS. 1–3) opens and closes the valve disc apertures 60 according to direction of solution flow as determined by direction of plunger movement. The valve diaphragm comprises an outer ring 66 fitted over the circumference of the disc for engagement with the inner surface of the barrel. The ring provides a seal 68 (FIG. 1) at this juncture. An annular diaphragm 70 integral with the ring extends radially inward and covers the front face of the valve disc including the apertures 60. It will be understood that the valve diaphragm opens to outward flow of solution through the apertures 60 into the annular chamber 58 and closes the apertures during inward flow of solution into the evacuator.

Figure 5:
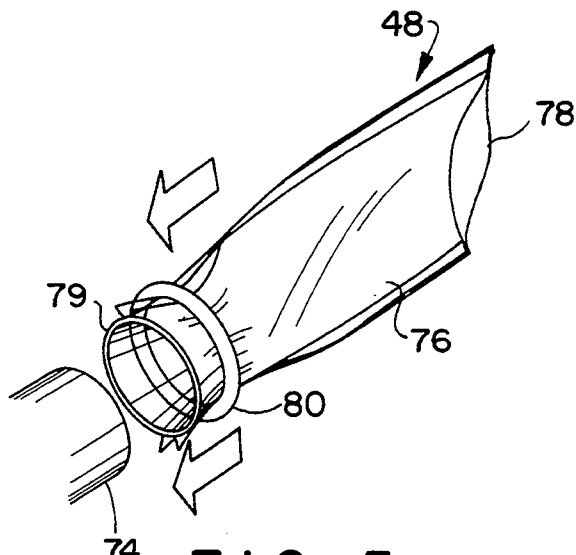
FIG. 5 is a perspective view of the inlet valve with valve flange assembly components.
Figure 6:
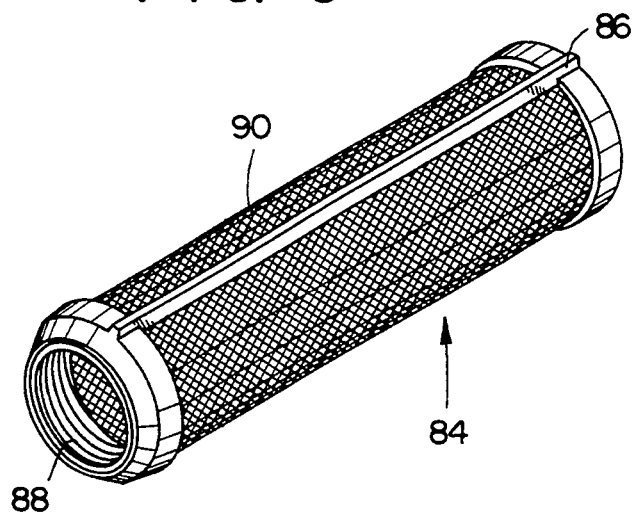
FIG. 6 is a perspective view of a tissue collection trap.

The valve flange further includes a rearwardly extending tubular section 74 (FIGS. 4b–5) further defining the central passageway and providing a mounting surface for a second control valve 48 in the form of a collapsible flapper valve 76. The flapper valve comprises a film tube open at one end 78 and secured at its other end 79 to the valve flange section 74 in a fluid tight manner as, for example by a securing ring 80. The flapper valve opens at end 78 for inward flow of solution to the interior of the barrel and closes by collapsing its film side walls when the contained solution is pressurized by depressing the plunger.

The valve flange further includes a rearwardly projecting collar 82 for positioning a tissue collection trap 84. In a preferred embodiment, the tissue collection trap comprises an open support frame 86 secured to the collar by a suitable removable connection such as threads 88. The support frame carries an outer generally cylindrical mesh screen 90 for passing solution from the interior passageway to the barrel chamber while trapping and collecting any tissue evacuated from the bladder. Because of the positive displacement provided by the plunger during evacuation, entrained tissue is carried along with the solution washing into the barrel chamber. The solution inflow pushes open the flapper valve carrying along entrained tissue which is then trapped and retained between the mesh and the flapper valve in the collection trap.

Figure 3:
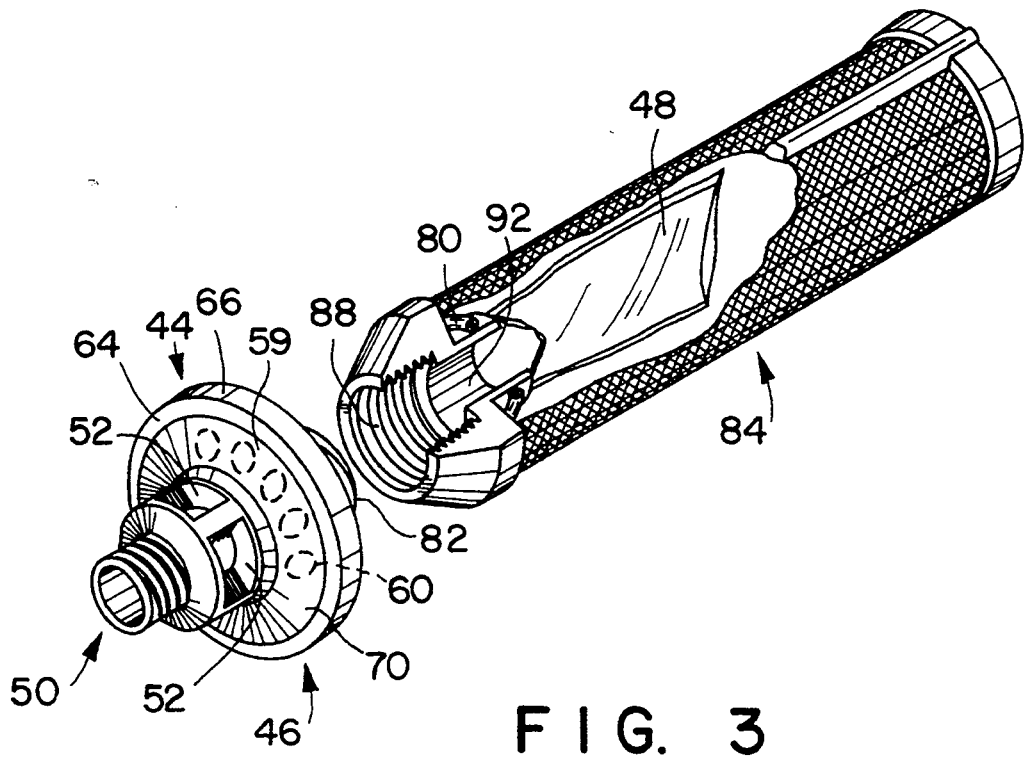
FIG. 3 is an enlarged perspective view partly in section of a modified arrangement of inlet valve and tissue collection trap for the evacuator.
Figure 4A:
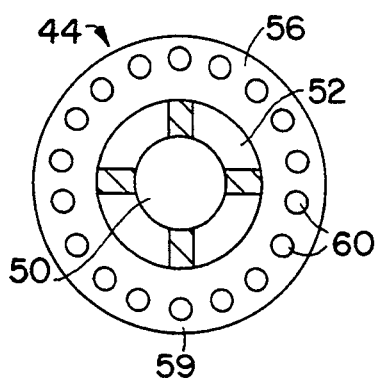
FIGS. 4a and 4b are front and side elevation views in section, respectively, of the valve flange forming part of the evacuator.
Figure 4B:
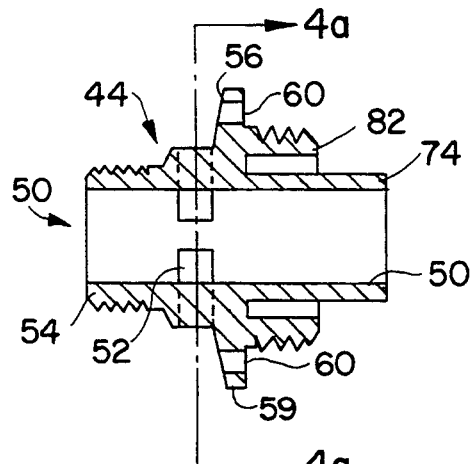

In another form of the collection trap 90 shown in FIG. 3, the flapper valve 48 is fitted to a collar 92 within the collection trap and serves the additional function of a closure for the trap confining tissue therein when the trap is removed from the evacuator. The flapper valve is retained on the collar by suitable means such as ring 80.

According to the invention, the collection trap can be removed, drained of solution, and shipped to a laboratory for analysis of collected tissue.

The inlet and outlet flows of solution are shown schematically in the drawing FIGS. 7 and 8. For inflow of solution, the plunger 16 is retracted or withdrawn in the direction of the arrow causing underpressure in the barrel chamber 61 and drawing solution through the nozzle 20 and central passageway 26. The first (outlet) control valve 46 closes as incoming fluid presses the diaphragm 64 against the valve apertures 60 thereby preventing backflow into the barrel chamber 61. Incoming fluid continues flow through the second control (inlet) valve 48, through the tissue trap and its mesh screen 84 filling the expanded interior volume 61 of the barrel chamber and the hollow interior 63 of the plunger. Tissue T entering the trap is retained therein by means of the mesh screen and the flapper valve 48 which will collapse and seal when overpressure is applied to the solution.

By depressing the plunger (FIG. 8) overpressure occurs and solution flows out of the evacuator returning to irrigate the bladder. As noted overpressure closes the flapper valve. The filtered return solution then passes out through the valve disc apertures 60, through the annular chamber 58 and ports 52 into the central passageway and out the nozzle. Plunger movement continues expelling filtered solution until the leading edge 17 of the plunger comes to rest against the rear face of the disc valve. In this position the tissue trap occupies the interior chamber of the plunger. By repeating the irrigation-evacuation cycle substantially all tissue fragments are trapped and collected for inspection and analysis.

FIG. 8 best illustrates the evacuator hollow plunger in its dual telescoping characteristic. The plunger telescopes within the syringe barrel and telescopes over the tissue collection container and inflow control valve located in the barrel. This compact and highly efficient arrangement provides for the irrigation and evacuation flow of the solution according to principles of positive displacement. By repeating the irrigation-evacuation cycle substantially all tissue fragments are trapped and collected in the mesh container for inspection and analysis.

The evacuator may be taken apart by removal of the plunger for access to the tissue container for analysis of the tissue. The container will drain of solution as it is removed from the syringe a feature of the invention that simplifies the task of retrieving the tissue for identification and shipment to a laboratory. Indeed, the tissue may be left untouched in the container for this purpose.

As a result of the unique dual telescoping characteristic, the evacuator has the same look and feel as well as ease of operation of a standard syringe. The invention results in a syringe which is simple and practical to use and which efficiently and quickly separates tissue from solution. Moreover, the evacuator can perform double use as a Toomey evacuator functioning as an irrigation syringe with or without a collection container.

In the foregoing specification, the evacuator is described with reference to use for a urological procedure. It will be clear that the evacuator is useful for other purposes involving irrigation/evacuation with or without a tissue trap. Moreover the design layout of the evacuator (particularly as to order of flow of fluid) is suitable for a range of evacuator sizes from 10 cc and larger.

I claim:

1. A syringe for irrigating a body cavity with a sterile fluid and evacuating fluid and entrained tissue from the cavity comprising a barrel having first and second openings at opposite ends thereof, a hollow plunger having first and seconds ends wherein said first end is slidably telescoped into the barrel through said first opening for drawing fluid into and expelling fluid from the barrel through said second opening, means for controlling the order of flow into and out of the barrel through said second opening, the controlling means positioned within said barrel adjacent to and in communication with said second opening, said controlling means defining an inlet path and an outlet path, an inlet valve positioned in the inlet path providing for influx of fluid into the barrel and preventing reverse flow through the inlet path, receiving and separating means within the barrel for receiving the influx through the inlet valve and for separating and collecting tissue entrained in the fluid, an outlet valve positioned in the outlet path providing for efflux of fluid from the barrel and for preventing the reverse flow through the outlet path, and the hollow plunger having an opening in said first end for receiving said receiving and separating means and for providing additional fluid volume within the syringe when the plunger is depressed into the barrel.

2. A syringe as defined in claim 1 in which the controlling means defines the inlet path along a central passageway extending through said second opening to the barrel interior, the inlet valve comprises a collapsible tube lying along the inlet path within the barrel for opening when the plunger draws fluid into the barrel and collapsing when the plunger expels fluid, the receiving and separating means comprises a mesh basket fitted to the control means and encompassing the inlet valve, and the outlet valve comprises a plurality of apertures located in the outflow path along the interior perimeter of the barrel and a valve diaphragm for closing the apertures when the plunger draws fluid, and for opening the apertures when the plunger expels fluid.

3. A syringe for irrigating a body cavity with a sterile fluid and evacuating fluid and entrained tissue from the cavity comprising a barrel having proximal and distal open ends, a hollow plunger having first and second ends wherein said first end is slidably telescoped into the barrel through the barrel proximal end for drawing fluid into and expelling fluid from the barrel through the distal end, means at the barrel distal end for controlling the order of flow into and out of the barrel open distal end, the controlling means defining an inlet path along the central axis of the barrel, an inlet valve fitted to the control means along the inlet path and allowing influx of fluid into the barrel and preventing reverse flow through the inlet path, receiving and separating means encompassing the inlet valve for receiving the influx and for separating and collecting tissue entrained in the fluid, the controlling means further defining an outlet path along the interior periphery of the barrel, the control means having an outlet valve providing for efflux of fluid from the barrel and for preventing the reverse flow through the outlet path, and the hollow plunger providing for additional fluid volume within the syringe and having an opening in said first end for accommodating the receiving and separating means when the plunger is depressed into the barrel.

4. A syringe for irrigating a body cavity with a sterile fluid and evacuating fluid and entrained tissue from the cavity comprising a generally cylindrical barrel having openings at opposite ends thereof, a hollow plunger having first and second ends wherein said first end is slidably telescoped into the barrel through one end for drawing fluid into and expelling fluid from the barrel through the other end, control means affixed to the barrel other end for controlling the order of flow into and out of the barrel, the control means defining an inlet path and an outlet path, an inlet valve in the form of collapsible tubular film fitted to the control means inlet path which opens when the plunger draws fluid into the barrel and which collapses when the plunger expels fluid from the barrel thereby preventing reverse flow through the inlet path, receiving and separating means for receiving the influx through the inlet valve and for separating and collecting tissue entrained in the fluid, the control means having an outlet valve in the form of a radially extending disc extending circumferentially along the interior perimeter of the barrel and having a series of longitudinally extending apertures forming part of the outlet path together with a valve diaphragm fitted to the outer circumference of the disc and having an annular diaphragm covering the outlet of each aperture and thereby providing for efflux of fluid from the barrel when the plunger expels fluid and for preventing the reverse flow through the apertures when the plunger draws fluid into the syringe, and the hollow plunger having an opening in said first end providing for additional fluid volume within the evacuator and for accommodating the receiving and separating means when the plunger is depressed into the barrel.

5. In a syringe for irrigating a body cavity with a sterile fluid and evacuating fluid and entrained tissue from the cavity having a barrel with an open rear end, a cylindrical wall extending from the open rear end to a forward shoulder, and a syringe nozzle extending from said forward shoulder, said syringe further including a hollow plunger with a closed end and an open end slidably telescoped into the barrel through the open rear end for drawing fluid into and expelling fluid from the barrel through said syringe nozzle, the improvement comprising; a valve flange for controlling the order of flow into and out of the barrel, the valve flange being positioned inside the barrel in spaced relation from the forward shoulder of the barrel, the valve flange having a central passageway defining an inlet path extending from the syringe nozzle to the interior of the barrel, the valve flange in cooperation with the barrel wall defining an outlet path, an inlet valve affixed to the valve flange providing for influx of fluid into the barrel and preventing reverse flow through the inlet path, a porous receptacle cooperating with the valve flange for receiving the influx through the inlet valve and for separating and collecting tissue entrained in the fluid, the valve flange further incorporating an outlet valve in the form of a disc projecting radially and circumferentially from the valve flange to occupy the outlet path between the valve flange and the barrel wall and to position a plurality of apertures through the disc along the outlet path, a valve diaphragm providing for efflux of fluid through the apertures when the plunger expels fluid and for preventing the reverse flow through the outlet path when the plunger draws fluid, the valve flange and barrel shoulder defining an annular chamber forming part of the outlet path and communicating with the central passage through a plurality of ports in the valve flange, and the valve flange extending through the open end of the hollow plunger when the plunger is telescoped into the barrel.

6. A syringe comprising a barrel, a hollow plunger having first and second ends wherein said first end is slidably telescoped into said barrel, said hollow plunger together with the barrel defining an interior chamber of the syringe, a nozzle at one end of the barrel for inlet and outlet of fluids, an inlet valve within the barrel communicating with the nozzle for admitting fluid to the chamber when the plunger creates underpressure in the chamber and for closing when the plunger creates overpressure in the chamber, and an outlet valve within the barrel communicating with the nozzle for closing when the plunger creates an underpressure in the chamber and for opening during overpressure for outflow of fluid from the chamber through the nozzle, and the hollow plunger having a opening in said second end for telescoping over the inlet valve when fully depressed into the chamber.

7. A syringe comprising a barrel, a hollow plunger having first and second ends wherein said first end is telescoped into said barrel, said hollow together with the barrel defining an interior chamber of the syringe, a nozzle at one end of the chamber for inlet and outlet of fluids, an inlet valve within the barrel communicating with the nozzle for admitting fluid to the chamber when the plunger creates underpressure in the chamber and for closing when the plunger creates overpressure in the chamber, and an outlet valve within the chamber communicating with the nozzle for closing when the plunger creates an underpressure in the chamber and for opening during overpressure for outflow of fluid from the chamber through the nozzle, a tissue collection trap within the barrel encompassing the inlet valve for separating tissue from fluid as the fluid is admitted to the chamber, and the hollow plunger having an opening in said second end for telescoping over the tissue collection trap when depressed into the chamber.

8. A syringe as defined in claim 7 in which the tissue collection trap is removable from the barrel.

9. A syringe as defined in claim 12 in which the inlet valve is secured within the collection trap and in which said tissue collection trap and inlet valve are removable as a unit from the barrel.

10. A syringe comprising a barrel, a hollow plunger telescoped therein and together with the barrel defining an interior chamber of the syringe, a nozzle at one end of the barrel for inlet and outlet of fluids, an inlet valve in the form of a collapsible, open ended film tube within the chamber communicating with the nozzle for admitting fluid to the chamber when the plunger creates underpressure in the chamber and for closing when the plunger creates overpressure in the chamber, and an outlet valve within the chamber communicating with the nozzle for closing when the plunger creates an underpressure in the chamber and for opening during overpressure for outflow of fluid from the chamber through the nozzle.

11. A syringe comprising a barrel having a cylindrical wall, a hollow plunger telescoped therein and together with the barrel defining an interior chamber of the syringe, a nozzle extending from said cylindrical wall at one end of the barrel for inlet and outlet of fluids, an inlet valve in the form of a collapsible, open ended film tube within the chamber communicating with the nozzle for admitting fluid to the chamber when the plunger creates underpressure in the chamber and for closing when the plunger creates overpressure in the chamber, and an outlet valve communicating with the nozzle for closing when the plunger creates an underpressure in the chamber and for opening during overpressure for outflow of fluid from the chamber through the nozzle, the outlet valve including a disc fitted in the chamber adjacent the nozzle and having a plurality of apertures and an annular diaphragm fitted over the periphery of the disc for sealing the disc interface with the barrel wall and for covering the plurality if apertures to prevent inflow and allow outflow from the chamber.

12. A syringe comprising a barrel having a cylindrical wall, a hollow plunger having first and second ends wherein the first end is telescoped into said barrel, said hollow plunger together with the barrel defining an interior chamber of the syringe, the barrel having a shoulder and nozzle extending from said cylindrical wall at the barrel forward end for inlet and outlet of fluids, means for controlling the order of flow into and out of the barrel being positioned inside the barrel in spaced relation from the forward shoulder of the barrel, the controlling means having a central passageway defining an inlet path extending from the syringe nozzle to the interior of the barrel, an inlet valve affixed to the central passageway providing for influx of fluid into the barrel and preventing reverse flow through the inlet path, a porous receptacle affixed to the central passageway and encompassing the inlet valve for receiving the influx through the inlet valve and for separating and collecting tissue entrained in the fluid, the controlling means further incorporating an outlet valve in the form of a disc projecting radially and circumferentially from the inlet passageway across an outlet path between the inlet passageway and the barrel wall, plurality of apertures providing an outlet path through the disc, means fitted to the disc for permitting efflux of fluid through the apertures when the plunger expels fluid and for preventing the reverse flow through the apertures when the plunger draws fluid, and the hollow plunger having an opening in said second end for telescoping over the order of flow controlling means.

* * * * *